United States Patent [19]

Cantor et al.

[11] Patent Number: 4,559,310
[45] Date of Patent: Dec. 17, 1985

[54] ASSAY METHODS AND SYSTEMS UTILIZING MAST CELL CLONES

[75] Inventors: Harvey I. Cantor, Boston; Gary Nabel, Cambridge, both of Mass.

[73] Assignee: Dana Farber Cancer Institute, Boston, Mass.

[21] Appl. No.: 496,543

[22] Filed: May 20, 1983

[51] Int. Cl.[4] .................. G01N 33/54; C12Q 1/29
[52] U.S. Cl. ............................ 436/519; 435/7; 435/29; 436/513; 436/808
[58] Field of Search ............ 436/513, 519, 808; 435/29, 7

[56] References Cited

PUBLICATIONS

Daëron, et al., Journal of Immunology, 129 (3), pp. 1212–1218 (1982).
"Basic and Clinical Immunology," D. P. Stites et al., eds., Lange Medical Publications, Los Altos, Ca., 1984 pp. 246–253.
Guyton, Textbook of Medical Physiology, 77 et seq. (5th Ed. 1976).
L. J. Roberts et al., Biochem. Biophys. Acta 575:185 (1979).
Nagas et al., Science 212:333 (1981).
F. Lui et al., J. Immunol. 124:2728 (1980).
Nabel et al., Cell 23:19 (1981).
Shaff et al., Anal. Biochem. 94:425 (1979).
Robinson et al., Biochem. J. 107:321 (1968).
Schwartz et al., J. Immunol. 126:2071 (1981).
H. Saito et al., J. Biol. Chem. 243:1536 (1968).
E. Razin et al., PNAS USA 79:4665 (1982).
Levine et al., PNAS USA 78:7692 (1981).
R.A. Lewis et al., Nature, 293, 103–107 (Sept. 1981).
G. Nabel et al., Nature, 291, 332–333 (1981).
S.J. Galli et al., J. Cell Biol, 95, 435–444 (Nov. 1982).
E. Razin et al., J. Biol. Chem., 257 (12) 7229–7236 (1982).

Primary Examiner—Sidney Marantz
Assistant Examiner—Louanne C. Krawczewicz
Attorney, Agent, or Firm—David G. Conlin; Ernest V. Linek

[57] ABSTRACT

The present invention is directed to an in vitro assay, useful in determining the effectiveness of anti-allergy compounds and/or useful in measuring the degree of sensitivity of a patient to particular allergens.

The present invention permits potential anti-allergy agents to be assayed in a number of ways. For example, the binding and dissociation rates of IgE to the mast cells in the presence and the absence of the substance being tested may be measured thereby giving a direct indication of that substance's ability to interfere with the IgE binding reaction. Another measure of a substance's potential as an anti-allergy agent is based upon the release of mediators or other compounds from the mast cells after sensitization by the allergen and exposure of the sensitized cells to the allergen.

The present invention generally involves the following steps:
(a) sensitizing cloned mast cells to an allergen;
(b) exposing sensitized mast cells to the allergen in the presence of a test anti-allergy agent; and
(c) measuring the reaction products of step (b) for an indication of test compound effect.

19 Claims, 2 Drawing Figures

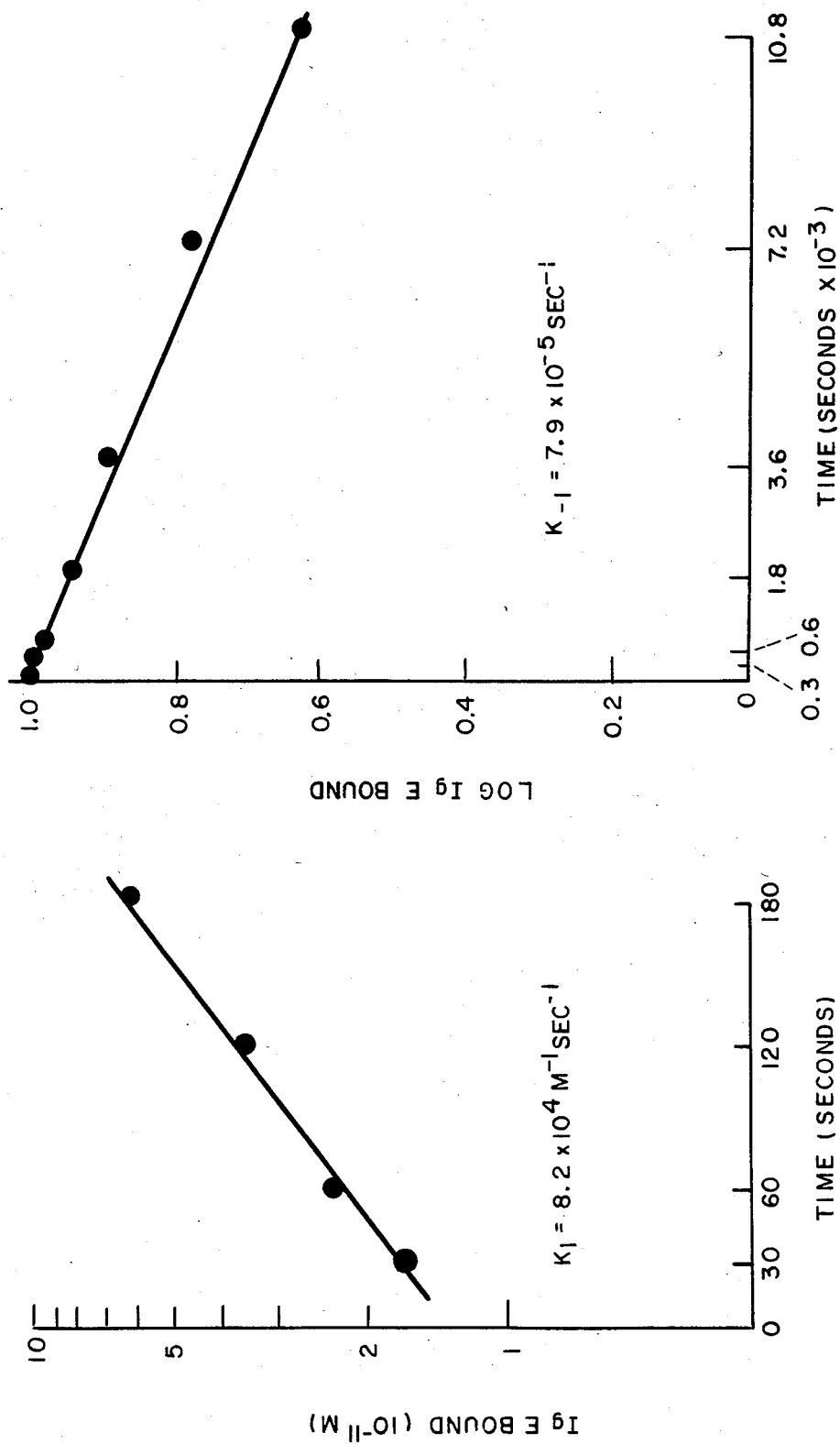

ASSAY METHODS AND SYSTEMS UTILIZING MAST CELL CLONES

BACKGROUND OF THE INVENTION

The invention relates to methods and systems for identifying methods and compositions which are effective in counteracting allergic reactions. More specifically, the present invention involves the use of cloned mast cells to test in vitro for the ability of compounds and compositions to interfere with the response of mast cells to allergens in vivo, by interference with the ability of mast cells to bind to IgE, by inhibition of the synthesis or secretion of allergic mediators, such as leukotrienes or prostaglandins by IgE-bound mast cells, or by deactivation of such mediators, e.g., by combination with or bonding to them.

Allergic persons or animals are afflicted with an over reaction of the body to the particular allergens to which the individual is allergic, such as pollen, dust, animal dander, etc. The allergic reaction is initiated by a stereospecific interaction involving the allergen, the mast cells and immunospecific materials which cause degranulation of the mast cells in the presence of the allergen, generally referred to in this application as immunoglobulins of the type IgE (also known as reagin or sensitizing antibodies). Binding to the IgE on the mast cell surface immunologically activates the mast cell, which then releases a variety of substances, including histamine, leukotrienes, and other components of what has traditionally been known as "slow reacting substance of anaphlaxis (SRS-A)," glycosoaminoglycans (e.g. heparin, chondroitin sulfate) serotonin, prostaglandins and/or other materials, depending on the type of mast cell involved. These substances affect the tissues in the locale of the affected mast cells, typically causing vasodilation, increased vasopermeability, non-vascular smooth muscle contraction, leucocyte infiltration, and destruction and repair of local tissue. See, e.g., R. A. Lewis, et al., "Mediation or Local Homeostasis and Inflammation by Leukotrienes and Other Mast Cell Dependent Compounds," Nature, 293:103 (1981), the disclosure of which is incorporated herein by reference.

The seriousness and type of the allergic reaction depends to some extent on the type and location of the mast cells involved. For example, when allergens are injected directly into the blood stream, the reaction can take place with mast cells located throughout the circulatory system. The release of histamine, leukotrienes, and other mediators, results in substantial vasodilation and loss of plasma flow. The affected individual can go into anaphylactic shock and die within minutes of the infusion of the allergen into the blood stream.

More localized instances of the allergic reaction include asthmatic attacks, where the allergen affects the tissue of the bronchioles in the lungs; "hay fever" symptoms of swelling and fluid leakage in the nasal tissues when the allergen contacts those tissues; and urticaria of skin tissues, resulting in "hives" when the allergen enters those tissues. Similar reactions can occur, with varying degrees of seriousness, where, because of infection, aging, or other factors, the body loses its immunological tolerance for its own tissues. In autoimmune diseases, the body's immunological defenses are activated against its own tissue, causing substantial destruction of the tissues involved. Autoimmune related diseases include rheumatic fever, acute glomerulonephritis, myasthenia gravis, and systemic lupus erythematosis. See, e.g., Guyton, Textbook of Medical Physiology, 77 et seq (5th Ed. 1976).

The treatment of chronically allergic individuals typically has been with antihistamines, to prevent or diminish the effect of the histamines released as a result of the allergic reactions. However, antihistamines are often ineffective against the actions of other mediator compounds released after the allergic reaction. Means have been lacking for identifying compounds which counteract such other mediators. Moreover, more effective materials for combating allergic type reactions described above can be developed by identifying those reagents which block the reaction between the allergen and the IgE receptors on the surface of mast cells, thus preventing the activation of such cells in the first place, which in turn prevents the release of histamine, leukotrienes, and other destructive mediator compounds. Until now, the only effective means for identifying the desired compounds has been through laborious, expensive, complicated bioassays, typically involving administration to lab animals, with subsequent analysis of reactions.

Another problem which has made treatment of allergies difficult is the inability to quantify sensitivity of mammals to allergens. Allergy specialists have not been able to accurately determine either the types of allergen to which individual mammals are sensitive, or the severity of the sensitivity, because prior to the present invention there was no accurate method to measure the precise degree of sensitivity to any particular antigenic material. Allergists have been left to crude skin tests, in which a variety of potential allergens are administered to an individual intradermally, and the existence and severity of allergic sensitivity is guesstimated from the appearance and size of the resultant wheals or erythema, i.e. area of the skin around the injection site which becomes inflamed after the injection of the allergen. Such tests are qualitative and subjective at best, and are not accurate, nor, in many cases, even repeatable.

BRIEF DESCRIPTION OF THE DRAWINGS

FIG. 1 is a graphical representation of the amount of IgE bound to mast cells of clone MC/9 versus time after contact, showing the determination of the binding rate constant, as discussed in Example 2.

FIG. 2 is a graphical representation of the dissociation rate and determination of the dissociation constant between IgE and mast cells of clone MC/9, as discussed in Example 2.

DESCRIPTION OF THE INVENTION

The present invention provides methods and systems for rapid determination of the effectiveness of various compounds for treatment of allergy, utilizing cloned mast cells. Preferably, the mast cells used are cells which have been cloned from fetal liver, or from lymph nodes. However, mast cell clones obtained from other sources, such as bone marrow or the peritoneal cavity, can also be used. Mast cells cloned from different tissues can be utilized in some instances in screening for compounds which counteract different mediator compounds. For example, mast cells from bone marrow, preferentially release leukotrienes, especially leukotriene $C_4(LTC_4$, i.e., 5(S),6(R)-5-hydroxy-6-S-glutathionyl-7,9-trans,11,14-cis-eicosatetraenoic acid) as compared to prostaglandins. Mast cells isolated from the peritoneal cavity, on the other hand, produce substantially more prostaglandins, e.g., $PGD_2$, than leukotrienes. L. J. Roberts et al., *Biochem. Biophys. Acta* 575:185 (1979), the disclosure of which is incorporated herein by reference.

The preferred mast cells are those cloned from fetal liver, e.g., fetal mouse liver, or from lymph nodes. These cloned cells, when exposed either to a calcium inophores or to IgE plus an appropriate antigen, release large amounts of leukotrienes and other mediators, usually within minutes. Leukotriene release of as much as 600–900 ng/$10^6$ cells has been observed. Most of the leukotriene released is $LTC_4$ although $LTB_4$ is also released in lesser amounts.

The present system permits potential anti-allergic agents to be assayed in a number of ways. The binding and dissociation rates of IgE to the mast cells in the presence and absence of the substance being tested may be measured, which gives a direct indication of that substance's ability to interfere with the IgE binding reaction. Also, the release of mediators or other compounds can be monitored after sensitization of the cells to antigen and exposure to the cells to that antigen.

By measuring the amount of mediators released by mast cells in the presence of a compound to be tested, the ability of that compound (a) to interfere with the interaction between IgE and the receptors for IgE on the surface of the mast cell, and/or (b) to otherwise inhibit the synthesis or release of mediators of allergic reactions such as leukotrienes and histamine may be determined. The ability to accurately monitor the individual mediators released on allergenic reaction of the mast cells makes it possible to detect valuable anti-allergic compounds or compositions which selectively inhibit production, secretion and/or action of particular mediators such as histamine or particular leukotriene or prostaglandins. Further, some mediators are often secreted faster than others, so that the assay can sometimes be shortened in time. Other means for measuring the effect of potential anti-allergy drugs or mast cell clones include the monitoring of release of certain acid hydrolases, such as beta-hexaminidase or beta-glucuronidase, production of which indicates degranulation of the mast cell clones via the IgE/allergen/IgE receptor interaction.

In another aspect of the present invention, mast cells can be used to determine the nature and degree of allergic sensitivity to particular allergens in individual mammals. The present invention allows quantification of particular allergic sensitivities, simply by incubation of a series of dilutions of the mammal's blood serum with mast cells in vitro, followed by challenge of those cells with the allergen of interest, after which the amounts of one or more mediator or marker compounds released by the mast cells are accurately measured. During incubation, IgE present in various concentrations in the serum which is directed to the allergen of interest, combines with the IgE receptors on the mast cell surface, so that then these cells are exposed to the allergen, the allergic reaction takes place, resulting in the release of the mediator compounds, such as histamine, leukotrienes, prostaglandins, etc., and/or marker compounds such as B-hexosaminidase. Using the assay, the degree of sensitivity to particular antigens can be precisely measured, in terms of the minimum concentration or titre of the serum which causes degranulation of the mast cells. This provides a measurement of the amount of reagin(s) contained in the serum, which in turn provides an indication of the degree of sensitization to the allergies involved. This assay provides a far more objective, quantitative evaluation of allergies than tests which have been previously available. By running a series of assays using different allergens, a complete, quantitative allergy profile of the subject mammal can be generated.

Where possible, it is preferred that the mast cells utilized in the present assays, particularly in the allergic sensitivity assay, be cells obtained or cloned from mammals of the same species as the one in whose allergic reactions are being tested. In that way, the maximum reactivity between the IgE of the test species and the IgE receptors of the mast cells used is ensured. Further, to provide maximum uniformity in the results, it is preferred that the mast cells utilized be cloned mast cells. Presently, the preferred mast cells for use in connection with the present invention are those cloned as described in G. Nabel, et al., *Nature* 291:332–4 (1981) and S. J. Galli et al., *J. Cell Biol.*, 95:435 (1982); the disclosures of which are both incorporated herein by reference. The references describe the establishment of fourteen mast cell lines from the liver of a mouse fetus, which cell lines were designated as mast cell Cl. MC/1–14. The cells have normal karyotypes, and can be cultivated in high numbers (greater than $10^6$ cells/ml). They are stable for at least 36 months, either alone or with a spleen cell layer. The doubling times in conconavalin A (Con A) range from about 36–48 hours; although those doubling times tend to increase when maintained in conditioned medium containing Con A conditioned with supernatant obtained from activated BALB/c spleen cells.

Using similar procedures, mast cell colonies can be isolated from adult mammalian spleen or bone marrow cells. Treatment of spleen or marrow cells with antisera to Thy 1.2 and complement facilitates growth of mast cell colonies, which by electron microscopy contain greater than 95%, usually greater than 99% mast cells, after 4–6 weeks of culture.

Mast cells cloned in accordance with the procedure should be maintained in the presence of a mast cell growth factor, such as that derived from cloned inducer T lymphocytes, as described in Nabel, et al supra.

Basically, the present invention involves (1) sensitizing cloned mast cells to a particular antigen, e.g. by incubating such cells with IgE which is specific to the antigen of interest, (2) exposing at least a portion of sensitized cloned mast cells, in the presence of any anti-allergic compound or composition to be tested, to the antigen (allergen) to which the cells have been sensitized, and (3) measuring (a) the binding and/or dissociation rate of the IgE to the mast cells, and/or (b) the amount of at least one indicator or marker compound which is secreted by the cloned mast cells in response to the allergen exposure. By "mediator" is meant a material which is secreted as a result of the allergenic reaction and which thereafter would normally take part in the body's response to such a reaction, such as histamine, leukotrienes, prostaglandins, etc. By "marker" is meant any other material which is secreted by mast cells in response to such allergenic reactions, but which is not usually considered as taking part in the body's immunological response to such reactions. An example of a marker for an allergic reaction by a mast cell is the enzyme beta-hexoseaminidase, secretion of which marks degranulation of cloned mast cells, but which may not particularly take part in the resulting inflammatory reactions.

Steps (1) and (2) should be accomplished in conditions which favor the viability of the mast cell clones. Preferably the IgE for sensitization and the antigen is added to the medium used for maintaining the mast cell clones, which contains suitable sera, sources of oxygen and nutrients, other factors which favor viability and growth, e.g., salts, growth factors, etc., and suitable conditions of pH and temperature, e.g. a pH of about 6.5-8, preferably about 7.0 to 7.5, and a temperature of about 0° C. to 60° C., preferably from about 15° C. to about 50° C., most preferably at about 37° C.

Suitable media for the culturing of cloned mast cells are known. Commercially available media include Dulbecco's Modified Eagle's medium (DME), Roswell Park Memorial Institute medium No. 1640 (RPMI 1640), and others are known. These preparations may advantageously be supplemented or used with serum, e.g. heat inactivated fetal calf serum (FCS), with other sources of energy or nutrition, e.g. glutamine, amino acids and/or with antibiotics, to prevent microbial infection.

Preferably the cloned mast cells are maintained in the presence of a growth/stimulation factor, of which several are known, including supernatant fluid taken from splenocytes stimulated with Con A, from cloned Lyl+2− inducer T lymphocytes (See Nabel et al., supra) or from WEHI-3 cells. See Nagas et al., *Science* 212:333 (1981), the disclosure of which is incorporated herein by reference. Most preferred is the mast cell growth factor obtained from cloned Lyl+2− inducer T cells.

Step 1 should be carried out for a period of time which is sufficient to ensure sensitization of the cells. Sensitization can take place for about 30 minutes to about 24 hours. Usually, sufficient sensitization with the IgE immunoglobulin takes place in from about 1 to 4 hours. The optimum amount of IgE used for sensitization will vary from case to case, but will typically run between 0.1 and 100 ug per $10^6$ cells, preferably about 5-15 ug/$10^6$ cells. The IgE immunoglobulins prepared against specific antigens are prepared in known manner, e.g. as disclosed by F. Lui, et al., *J. Immunol.* 124:2728 (1980), the disclosure of which is incorporated herein by reference. These antibodies can be raised against a wide variety of antigens of haptans, the particular antigen described by Lui being dinitrophenol (DNP), that haptan being bound to proteins, such as bovine serum albumin (DNP-BSA). The amount of antigen to be added may generally be lower than the amount of IgE used to sensitize the cells. Generally between 0.1 and 1,000 ng/$10^6$ cells may be utilized; preferably from about 1 to about 50 ng/$10^6$ cells. Most preferably about about 15-30 ng of antigen or allergen are used per $10^6$ cells.

Most mediator compounds are secreted rather rapidly after the allergic reaction takes place. Accordingly, a time of 5 to 10 minutes after admixture of the IgE sensitized mast cells, the antigen to which the IgE is inserted and any compound to be tested, will normally be sufficient to permit substantial secretion of mediator and/or marker products. This time period may vary for different mast cell clones, however. A standard testing time should be chosen for each different mast cell clone system used. As noted above, the optimum testing time may also vary somewhat depending on the particular mediators or markers which are of interest.

The amount of material to be tested as anti-allergy agents will vary depending on the anticipated potency of the drug. Generally a physiological dose response curve should be generated for materials to be tested, in concentrations ranging from picograms per milliliter up to any desired concentrations which are non-toxic to mammals to be treated. Generally, the range of about 1 pg/ml to about 10 ug/ml will be adequate to test a given compound's ability to block or otherwise interfere with the mediators secreted by mast cells as a result of the allergic reaction.

The mast cell line presently preferred for use in the assay of the present invention is clone MC/9, cloned as described in Nabel et al., *Cell* 23:19 (1981). A sample of this mast cell line has been deposited at the American Type Culture Collection, and has been given the accession number ATCC CRL8306.

If desired, the testing system of the present invention can be supplied in the form of a kit, the components of which comprise a vial containing the mast cell clone to be utilized, contained in a medium which comprises essential nutrients, energy sources, growth factors, etc., a vial containing the IgE antibody for sensitization of the mast cells, in non-denaturing solution, such a vial containing the antigen or haptan to which the antibody is directed, also in a non-denaturing medium. A vial of medium suitable for maintaining the cell line, and vials containing the reagents used to analyze for the mediator/marker compounds of interest, may also be provided. The mast cells can conveniently be provided in frozen form, in which case revitalization by appropriate known thawing procedures will be required before use. Where the assay is being used to test for particular allergies in individual mammals, the vial containing IgE sensitized to the allergen(s) of interest is not a required part of the kit, but may be provided as a control.

In use, the cloned mast cells are preferably washed free of growth factors and other extraneous material and resuspended in suitable medium. The preferred amount of cells used is $10^5$ to $10^6$ cells/ml of suitable medium. The source of IgE antibody, either IgE raised to antigens of interest, or cell free serum from the animal whose sensitivity is to be determined, is then added to the mast cell suspension, and the cells incubated with the antibodies for a period of time sufficient to sensitize them, e.g., 15 minutes to 1 hour. Preferably the source of IgE provides from about 0.01 to 100 ug of IgE per milliliter, more preferably about 0.1-10 ug/ml. About 5 ug/ml of Ige will normally provide sufficient material to the mast cell receptors to allow significant reaction to take place. The cells are then preferably washed free of unbound IgE prior to admixture with the compound to be tested, preferably in various dilutions as described above, and the appropriate antigen. Preferably, a control sample of cells without the anti-allergy compound of interest, may also be run. In the case of the allergic sensitivity assay, a control sample using IgE specific to the antigen of interest may also be useful. After a brief period of incubation of the resulting admixture, e.g. 1 to 60 minutes, typically about 5-10 minutes, the supernatant fluid is removed and analyzed for secreted mediator and/or marker materials.

The amounts of secreted mediators and/or markers can be determined using known procedures. For example, the various leukotrienes and prostaglandins can be analyzed by radioimmunoassay (RIA) or chromatographic techniques, e.g., high pressure liquid chromatography. Histamine can likewise be determined by radioenzymatic assay, see Shaff, et al., *Anal. Biochem.* 94:425 (1979), or by a simple fluorometric analysis, using commercially available systems such as the Autoanalyzer II, sold by Technicon. Enzymatic markers like B-hexosaminidase can be analyzed by reaction with known amounts of their specific substrates. See, e.g., Robinson, et al., *Biochem J.* 107:321 (1968); Schwartz et al., *J. Immunol.* 126:2071 (1981). Glycosoaminoglycans may be analyzed in accordance with known enzymatic/chromatographic methods. See, e.g., H. Saito et al., *J. Biol. Chem.* 243:1536 (1968). The disclosure of these references is incorporated herein by reference.

Materials to be tested include known or potential pharmaceuticals for treatment of allergies, including, for example, ethanolamine derivatives, such as carbinoxamine maleate, diphenhydramine hydrochloride, doxylamine succinate; ethylenediamine derivatives, such as chlorothen citrate, methapyrilene hydrochloride, pyrilamine maleate, tripelennamine citrate; phenothiazine derivatives, e.g. cyproheptadine hydrochloride, methadilazine hydrochloride, trimeprazine tartrate; propylamine derivatives, e.g., brompheniramine maleate, chlorpheniramine maleate, dexbrompheniramine maleate, dexchlorpheniramine maleate, dimethindene maleate, pheniramine maleate, pyrrobutamine phosphate and triprolidine hydrochloride and other anti-allergic compound, e.g. steroids such as glucocorticoids, as well as compounds which are chemically similar to these compounds.

The following illustrative embodiments are not to be taken as limitive, but merely as illustrating examples of applications of the invention. In this application, the Greek letters alpha, beta, delta and mu are represented by the figures a̲, B̲, D̲ and u̲, respectively.

EXAMPLE 1: PREPARATION OF MAST CELL LINE

The liver of a 13 day old mouse fetus from one A/J female mated with a C57BL/6 male are incubated in Dulbecco's Modified Eagle's Medium (Gibco) modified with 4% heat-inactivated fetal calf serum, $5 \times 10^{-5}$M 2-mercaptoethanol and 2 mM glutamine (MEM) conditioned by concanavalin A (Con A)-activated BALB/c spleen cells (Con A-CM). Ten days later, cells are distributed at limiting dilutions in wells containing irradiated (2,000 R) syngeneic bone marrow cells. Colonies appear at 10–14 days with a cloning efficiency of approximately 10%. All colonies grown under these conditions are composed of cells that resemble mast cells by light microscopy because of their prominent metachromatic cytoplasmic granules. All colonies express the Ly 5+ Thy 1,Ly1−2− phenotype of surface membrane glycoproteins. No growth of mast cells is observed from preparations of irradiated bone marrow cells.

Mast cell lines are cloned, as disclosed in Nabel et al., *Cell* 23:19–23 (1981), the disclosure of which is incorporated herein by reference, by micromanipulation and have been designated Cl.MC/1-14. The cloned cells have normal karyotypes and can be cultivated in large numbers ($>10^8$) with doubling times in Con A-CM of 36–48 h. Clones are stable for at least 36 months, either alone or with an irradiated spleen cell feeder layer, although doubling times of cells maintained in Con A-CM may progressively increase.

Using similar conditions, mast cell colonies also may be isolated from adult spleen, lymph gland or bone marrow cells or other tissues. Treatment of spleen or marrow cells with antiserum to Thy 1.2 and complement facilitates growth of mast cell colonies, which by electron microscopy contain >95% (usually >99%) mast cells after 4–6 weeks of culture. The mast cell lines can be maintained with medium conditioned by Con A-stimulated splenocytes (Con A-CM), cloned Ly 1+2− inducer T lymphocytes, or WEHI-3 cells.

EXAMPLE 2: SENSITIZATION OF MAST CELLS WITH IgE

Cells from the above described cell line are washed and resuspended in DME or RPMI-1640 medium plus 0.01M EDTA and 10% fetal calf serum, pH 7.4, at $1-30 \times 10^5$ cells/ml. Cells in 0.4 ml received 0.05 ml of additional medium containing 10 mg/ml of noniodinated, affinity purified mouse monoclonal IgE which is sensitized to dinitrophenol-bovine serum albumin (DNP-BSA) in the manner disclosed by Liu et al., *J. Immunol.* 124:2728–2737 (1980), the disclosure of which is incorporated herein by reference. The monoclonal IgE antibody is obtained from hybridoma cell line H 1 DNP-a-26, as described by Liu et al. After 15 minutes, at 37°C., 100 ug/ml of radioiodinated IgE ($^{125}$I-IgE) sensitized to DNP-BSA is added to the sensitized cells in 0.05 ml and incubated for 90 minutes at 37°C., with constant shaking.

Duplicate determinations of binding of $^{125}$I-IgE to cells are made by layering 0.2 ml aliquots of cells onto 0.2 ml of heat-inactivated FCS and centrifuging the tube in a microfuge. The radioactivity in the cell pellets is measured in a gamma counter and the number of $^{125}$I-IgE molecules bound per cell calculated according to the formula:

$$N = \frac{CPM_0 - CPM_x}{CPM_E} \times \frac{3.2 \times 10^7}{\text{No. of cells}} \quad (1)$$

where N is the number of IgE molecules bound per cell, $CPM_0$ is the means counts per minute observed in cells without excess noniodinated IgE. $CPM_x$ is the mean counts per minutes observed in cells with excess noniodinated IgE (nonspecific binding) and $CPM_E$ is the number of counts per minute given by one nanogram of the $^{125}$I-IgE.

The formula rate constant ($K_1$) of IgE binding to MC/9 is measured by incubating prewarmed cells ($1.3 \times 10^6$/ml) with 3 ug/ml of $^{125}$I-labeled mouse monoclonal IgE at 37°C. in Dulbecco's modified Eagles medium containing 10% fetal calf serum and 0.01 mM EDTA with constant shaking. The binding reaction is stopped at various intervals by adding a 133-fold excess of unlabelled IgE. Cells in control tubes are incubated with a 133-fold excess of unlabeled IgE before addition of $^{125}$I-IgE. Non-specific binding of radioactivity to control cells is subtracted from experimental tubes to determine specific binding. The results are indicated in FIG. 1. The binding rate constant is about $8.2 \times 10^{-4} M^{-1} sec^{-1}$. The number of IgE receptors per cell is determined separately by incubating the cells with 10 ug/ml of $^{125}$I-IgE for 90 min. as described above.

To measure the dissociation constant rate ($K_{-1}$) of IgE bound to MC/9, cells ($1.3 \times 10^6$/ml) are incubated with 3 ug/ml of $^{125}$I-labeled mouse monoclonal IgE at 37°C. for 1 hr in Ly 1+2− T lymphocyte-conditioned Dulbecco's modified Eagles medium as described above. Cells are then divided into two tubes, centrifuged, and resuspended in fresh medium. A 133-fold molar excess of unlabeled IgE or an equal volume of culture medium is added to each tube at $t_0$. The cells are incubated at 37° C. with constant slow rotation and residual cell-bound $6_{125}$ I-IgE is determined at various intervals. The results are depicted in FIG. 2. The dissociation rate constant in this instance is about $7.9 \times 10^{-5}$ sec$^{-1}$.

EXAMPLE 3: TESTING OF INHIBITION FOR IgE BINDING

Example 2 is repeated, except that, prior to addition of labeled or unlabeled IgE, the cells are incubated at 37° C. for 15 minutes with various dilutions of the compound to be tested, e.g., tripelennamine citrate, in DME with 0.01M EDTA and 10% FCS, pH 7.4. Separate trials are run at the following concentrations of tripelennamine citrate: 1 ug/ml, 50 ng/ml, 1 ng/ml and 1 pg/ml.

Comparison of the binding and dissociation rate constants for IgE in the presence of the tripelennamine citrate, as compared with the binding and dissociation constants obtained in Example 2 gives a direct measure of the ability of that compound to interfere with the binding of IgE to IgE receptors on mast cells.

EXAMPLE 4: ANTIGEN INDUCED, IgE MEDIATED RELEASE OF COMPOUNDS

The mast cells described above are sensitized with IgE and exposed to antigen, and the mediator compounds produced are analyzed by the methods described in E. Razin et al., *PNAS USA* 79:4665 (1982), the other references cited herein, or by other known procedures. $10^5$ cells/ml of the mast cell clone described in Example 1 are suspended in 0.2 ml of Tyrode's buffer containing 0.32 mM of calcium ions, 0.2 mM magnesium ions and 0.5% gelatin (modified Tyrode's) and sensitized by incubation for 1 hour at 37° C. and 10 ug of mouse monoclonal IgE specific for DNP-BSA.

Sensitized cells are washed with 2 ml modified Tyrode's buffer, sedimented at 400 g at room temperature, and suspended in 0.5 ml of prewarmed 37° C. modified Tyrode's buffer containing 20 ng of DNP-BSA (18 mols of DNP/mol BSA). Reactions are stopped at five minutes after contact with antigen by addition of EDTA to give a concentration of 2 mM and centrifugation at 400 g for 5 minutes at room temperature. The supernatants are collected and the cell pellets are suspended in 1 ml of 10 mM Tris-HCl, 1M NaCl, pH 7.4 and sonicated at 4° C. with a Branson sonifier (setting 3, 50% pulse cycle, 10 pulses). Both the supernatants and the disrupted cell pellets should be assayed for their content of various mediators, as described below. A sample using mast cells which were not sensitized with IgE before exposure to DNP-BSA should be run as a control.

Histamine may be measured fluorometrically using an Autoanalyzer II (Technicon) equipped to detect histamine in the 0-10 ng/ml range. As an alternative, histamine can be measured by a radioenzymatic assay using $^3$H-labeled histamine, methyl $^{14}$C-labeled S-odenosyl-L-methionine (New England Nuclear) and rat kidney histamine methyltransferase. See R. A. Shaff et al., *Anal. Biochem.* 94:425 (1979). B-Hexosaminidase is assayed by hydrolysis of p-nitrophenyl-B-D-2-acetamido-2-deoxyglucopyranoside (Sigma); 1 unit of enzyme cleaves 1 umol of substrate/h at 37° C.

For quantitation of chondroitin sulfate E proteoglycan, bone marrow-derived mast cells ($1 \times 10^7$) are preincubated for 4 h at 37° C. in 10 ml of enriched medium containing 50-100 uCi [$^{35}$S]sulfate/ml (New England Nuclear Corp). Radiolabeled mast cells are sedimented at 400 g for 5 min at room temperature and washed with enriched medium. The cells are then sensitized with monoclonal IgE and challenged with DNP-BSA under the same experimental conditions as for unlabeled cells. After separation of the supernatant, intracellular $^{35}$S-labeled glycosoaminoglycans or proteoglycans are liberated at 4° C. by the addition of 0.1 ml of a solution containing 1% Zwittergent 3-12 detergent (Calbiochem-Behring Corp.) 0.1M 6-aminohexanoic acid, 0.1M sodium EDTA, 5 mM benzamidine HCl, 1 mM sodium iodoacetamine, 0.1M sodium aetate, pH 6.0, followed 30-60 sec. later by the addition of 1 ml of 4M guanidine hydrochloride (GnHCl) containing the same protease inhibitors. The $^{35}$S-labeled macromolecules released and those remaining cell-associated are both quanitated by measurement of radioactivity with a Searle Beta Counter (Model 6880, Searle Analytic).

The net percentages of release of histamine, B-hexosaminidase and $^{35}$S-labeled chondroitin sulfate $\bar{E}$ proteoglycan are calculated by the following formula;

$$\text{Net percent release} = \frac{S - S \text{ control} \times 100}{(S + P) - S \text{ control}}$$

where S=mediator content of supernatant of stimulated cells, P=mediator content of pellet of stimulated cells, and S control=mediator content of supernatant of unstimulated cells.

Generation of the sulfidopeptide leukotrienes is quantitated with radioimmunoassay (RIA). The supernatants are diluted to 100 ul with 10 mMTris-HCl, 0.15M NaCl, and 0.1% gelatin, pH 7.3 (Isogel buffer); mixed with 50 ul of buffer containing 5000-7000 cpm of $^3$H-labeled LTC$_4$ (New England Nuclear) and 100 ul of class-specific rabbit immune plasma; and incubated for 1 h at 37° C. $^3$H-labeled LTC$_4$ bound to the rabbit antibodies is precipitated by an overnight incubation at 4° C. with 200 ul of goat anti-rabbit IgG. The precipitates are pelleted by centrifugation, solubilized in 0.1N NaOH, and counted. Synthetic LTC$_4$ is detectable on the linear portion of a net radioligand binding inhibition curve over a dose range from 0.1 to 1.0 ng. See Levine et al., *PNAS USA* 78:7692 (1981), the disclosure of which is incorporated by reference. Because unstimulated cells do not generate immunoreactive leukotrienes, the antigen-induced release of leukotrienes may be expressed as ng of product released into the supernatant/$10^6$ cells.

For quantitation of PGD$_2$, supernatant diluted to 100 ul in Isogel buffer is mixed with 50 ul of buffer containing 6000 cpm of $^3$H-labeled PGD$_2$ (New England Nuclear) and 100 ul of rabbit anti-PGD$_2$ immune plasma for 1 h at 37° C. Normal rabbit plasma (100 ul) and goat anti-rabbit IgG antiserum (200 ul) are successively added, samples precipitated overnight at 4° C. and centrifuged. The pellets were resolubilized in 0.1N NaOH and counted. Synthetic PGD$_2$ is detectable on the linear portion of a net radioligand binding inhibition curve over a dose range from 0.1 to 2.0 ng. See Levine et al., supra. Antigen-induced release of PGD$_2$ may be expressed as ng of product released into the supernatant/$10^6$ cells; release from unstimulated cells should not be measurable.

The radiolabeled proteoglycans released into the medium and those remaining associated with the cells can also be characterized by gel filtration chromatography on Sepharose CL-4B and, after purification by cesium chloride density gradient sedimentation, by the disaccharide content of their bound glycosaminoglycans, as disclosed in Razin et al., supra, and Razin et al., *J. Biol. Chem,* 257:7229, the disclosure of which is incorporated herein by reference.

Within about 5-10 minutes after exposure of sensitized bone marrow derived mast cells to antigen, the cells release B-hexosaminidase, histamine, sulfodipeptide leukotriene, proteoglycans, and small amounts of prostaglandin $PGD_2$.

Mediator and marker compounds will similarly be released from sensitized, antigen-exposed mast cells obtained from other sources, such as the fetal liver mast cell clone described above, or mast cells derived from mammalian, including human, liver, lymph nodes or other bodily tissues.

EXAMPLE 5: EVALUATION OF EFFECT OF ANTI-ALLERGY COMPOSITIONS ON MEDIATOR AND MARKER RELEASES

The steps of Example 4 are repeated, except that, prior to challenge of the sensitized mast cells are incubated for 30 minutes in modified Tyrode's buffer containing 1 pg/ml, 1 ng/ml, 50 ng/ml, 1 ug/ml and 10 ug/ml, respectively of the compound or composition to be tested for its anti-allergy properties, e.g. doxylamine succinate.

About 5-10 minutes after challenge of the sensitized cells with DNP-BSA antigen, the reaction is stopped and the supernatant and disrupted cell pellets are assayed for their contents of mediator and marker compounds. Lack of secretion of significant amounts of mediators or markers indicates that the anti-allergy agent being tested interferes with the interaction of the antigen, the mast cell and the IgE or other material which fosters degranulation of mast cells. Lack of secretion of significant amounts of individual mediators or markers indicates that the anti-allergy compound or composition being tested interferes with the synthesis and/or secretion of those particular mediators or markers, or reacts with or otherwise interferes with the action of those mediators or markers.

In a similar way, the assay can also be used to measure the ability of test compounds to prevent degranulation of mast cells by non-immunospecific agents, e.g. calcium ionophores, e.g. calcium ionophore A23187. See, e.g., Razin et al. *PNAS USA* 79:4665 (1983) supra.

EXAMPLE 6: TESTING OF ALLERGIC SENSITIVITY

The procedure of Example 4 is repeated, except that, instead of IgE specific for DNP-BSA, the cells are suspended in 0.2 ml of modified Tyrode's buffer, and sensitized by addition of 0.2 ml of cell free mouse serum and incubated for 1 hour at 37° C. As a result of this incubation, the cells will be sensitized for any allergen to which the donor of the serum is allergic, since the reagins for such allergens are carried in the serum used.

In order to determine how much IgE to a particular allergen is contained in the subject serum (i.e., how allergic the subject is to that allergen), the above procedure is repeated with various dilutions of the serum in a non-denaturing diluent such as Tris-HCl (pH 7.5), e.g. 1 to 1, 10 to 1, 50 to 1, 100 to 1, 500 to 1, 1000 to 1, 5000 to 1, and 10,000.

The mast cells sensitized with these various dilutions of serum are then washed with 2 ml of modified Tyrode's buffer, and suspended in 0.5 ml of prewarmed 37° C. modified Tyrode's buffer containing 20 ng of the allergen of interest. After a desired period of time, e.g. 10 minutes, the reaction is stopped by addition of EDTA, the cells sonicated, if desired, and the supernatants and cell residues tested for mediator content as in Example 4. The determination of the lowest concentration of serum which gives an allergic reaction confirms an allergy to the specific allergen tested, and gives a quantitative measurement of the strength of sensitivity to that allergen.

The analytical techniques for measurement of released mediator and/or marker compounds provide a far more precise determination of sensitivity to particular antigens than the measurement of the size of wheals or erythema surrounding the point of infusion of the allergen into the skin by a scratch test or intradermal injection. Moreover, the sensitivities of different types of mast cells can be measured, so that, for example, allergens which might affect the tissues of the bronchioles, but not skin tissue, can be determined by the present assay.

Accordingly, the present invention provides assay systems of unprecedented sensitivity and specificity, for determining the effectiveness and mode of action of anti-allergy compounds or compositions used to treat or prevent harmful allergic or antigenic reactions in mammalian tissue.

While the details and advantages of the disclosed embodiments have been described with particularity, other embodiments will be readily apparent to the skilled in the art from a consideration of the present disclosure or from practicing the invention disclosed herein. The embodiments discussed in the specification are to be considered exemplary only, and the true scope of the invention should be determined by a consideration of the appended claims.

We claim:

1. A method of testing a material for its use in preventing allergic reactions in mammalian tissue, comprising: (a) sensitizing cloned mast cells in vitro with an immunoglobulin directed to a selected allergen; (b) admixing the resulting sensitized mast cells with the material to be tested; (c) contacting the sensitized mast cells with the allergen; and (d) determining, from the products of admixture, whether an immunoglobulin/allergen/mast cell reaction has occurred.

2. The method of claim 1, wherein the occurrence of an antigen/immunoglobulin/mast cell reaction is detected by measuring the binding of the immunoglobulin to the mast cells.

3. The method of claim 1, wherein the occurrence of an antigen/immunoglobulin/mast cell reaction is detected by analysis of the products of admixture for mediator or marker compounds.

4. The method of claim 3, wherein the products of admixture are analyzed for histamine, leukotrienes, B-hexoseaminidase, prostaglandins, glycosoaminoglycans or proteoglycans.

5. The method of claim 1, wherein the products of admixture are analyzed for B-hexosaminidase or B-glucuronidase.

6. The method of claim 1, wherein the mast cells are cloned from liver, lymph nodes, bone marrow or bronchiolar peritoneal tissue.

7. The method of claim 1, wherein the mast cells are cloned from the same species of mammal as that which produces the immunoglobulin.

8. The method of claim 1, wherein the mast cells are cells of clone MC/9.

9. The method of claim 1, wherein the sensitization takes place by incubation of the mast cells in a physiologic solution containing about 0.1 ug of immunoglobulin IgE per $10^6$ mast cells, for a period of from about 30 minutes to 24 hours, at a pH of about 6.5–8 at a temperature of from about 15° C. to 50° C.

10. The method of claim 9, wherein the mast cells are contacted with the material to be tested in an amount of 1 pg to 10 ug per $10^6$ cells.

11. The method of claim 10, wherein the mast cells are contacted with antigen in an amount of about 6.1 to about 1,000 ng/per $10^6$ mast cells.

12. A method of testing a mammal for allergic sensitivity to a selected allergen, comprising treating cloned mast cells in vitro with a serum from the mammal, admixing the resulting treated mast cells with the allergen, and determining, from the products of admixture, whether an allergic reaction has occurred.

13. The method of claim 12, wherein the occurrence of an allergic reaction is determined by analysis of the products of admixture for mediator or marker compounds.

14. The method of claim 12, wherein the occurrence of an allergic reaction is determined by analysis of the products of reactions of the treated mast cells and the antigen for the presence of secreted histamine, leukotrienes, B-hexoseaminidase, prostaglandins and glycosoaminoglycans.

15. The method of claim 12, wherein the mast cells are cloned from liver, lymph nodes, bone marrow, bronchiolar or peritoneal tissue.

16. The method of claim 12, where the mast cells are cloned from a mammal of the same species as that being tested.

17. An assay kit for testing a material for its ability to prevent allergic reactions in mammalian tissue, comprising a vial containing cloned mammalian mast cells in a physiologically acceptable medium, a vial containing a source of immunoglobulin which is reactive to an antigen and a vial containing the antigen.

18. The kit of claim 17, wherein the mast cells are frozen.

19. An assay kit for testing a mammal for allergic sensitivity, comprising a vial containing cloned mammalian mast cells in a physiologically acceptable medium, a vial containing the antigen of interest, and a reference standard comprising a source of IgE directed to the antigen.

* * * * *